United States Patent
Burwell

(10) Patent No.: US 6,790,369 B1
(45) Date of Patent: Sep. 14, 2004

(54) APPARATUS AND METHOD FOR PROTECTING TOROIDAL CONDUCTIVITY SENSORS

(75) Inventor: David C. Burwell, Ewa Beach, HI (US)

(73) Assignee: Universtiy of South Florida, Tampa, FL (US)

( * ) Notice: Subject to any disclaimer, the term of this patent is extended or adjusted under 35 U.S.C. 154(b) by 0 days.

(21) Appl. No.: 10/248,367

(22) Filed: Jan. 14, 2003

Related U.S. Application Data

(60) Provisional application No. 60/319,102, filed on Jan. 28, 2002.

(51) Int. Cl.[7] ............................................. B01D 35/02
(52) U.S. Cl. ...................... 210/747; 201/746; 201/767; 201/251; 73/53.01; 73/64.56
(58) Field of Search ............................. 210/739, 746, 210/747, 767, 251; 73/53.01, 64.56

(56) References Cited

U.S. PATENT DOCUMENTS

| | | |
|---|---|---|
| 4,375,199 A | 3/1983 | Graeme-Barber et al. |
| 4,415,858 A | 11/1983 | Hale |
| 5,271,819 A | 12/1993 | Bockowski |
| 5,344,606 A | 9/1994 | Brimmer |
| 5,354,603 A | 10/1994 | Errede et al. |
| 5,420,432 A | 5/1995 | Manook et al. |
| 5,474,664 A | 12/1995 | Thompson |
| 5,562,822 A | 10/1996 | Furness, Jr. et al. |
| 5,620,597 A | 4/1997 | Andelman |
| 5,662,805 A | 9/1997 | Cameron et al. |
| 5,676,820 A | 10/1997 | Wang et al. |
| 5,779,891 A | 7/1998 | Andelman |
| 5,858,219 A | 1/1999 | Kusmierz et al. |
| 5,864,140 A | 1/1999 | Owens |
| 5,889,209 A | 3/1999 | Piedrahita et al. |
| 5,929,453 A | 7/1999 | Andrews et al. |
| 5,951,869 A | 9/1999 | Heskett |
| 6,016,102 A * | 1/2000 | Fortune et al. ............... 73/46.3 |
| 6,185,988 B1 | 2/2001 | Baxter, Jr. |

* cited by examiner

Primary Examiner—Robert James Popovics
(74) Attorney, Agent, or Firm—Ronald E. Smith; Smith & Hopen, P.A.

(57) ABSTRACT

A submerged sensor head is protected from fouling by marine organisms by positioning the sensor head in a submerged hollow enclosure. Openings are formed in the hollow enclosure to admit water but filters are positioned in the openings so that only filtered water may enter the enclosure. The filters remove biologically active marine organisms from the water and have sufficient surface area to enable free flow of water into the hollow enclosure.

11 Claims, 2 Drawing Sheets

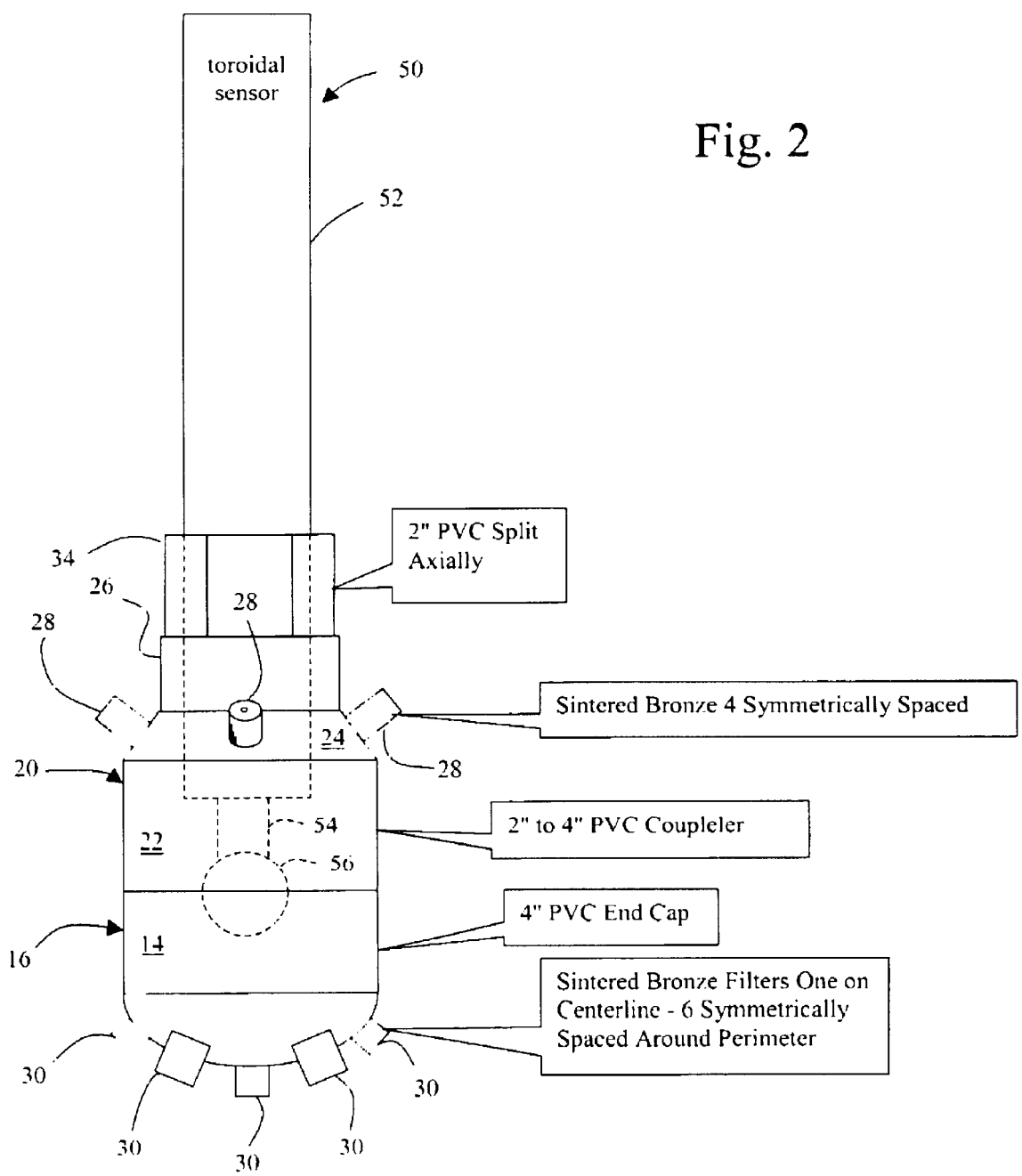

APPARATUS AND METHOD FOR PROTECTING TOROIDAL CONDUCTIVITY SENSORS

CROSS-REFERENCE TO RELATED APPLICATION

This application claims priority from U.S. provisional application Ser. No. 60/319,102, entitled: "Apparatus and Method for Protecting Toroidal Conductivity Sensors", filed Jan. 28, 2002.

BACKGROUND OF INVENTION

1. Field of the Invention

This invention relates, generally, to salinity measurements in near shore or estuarine environments. More particularly, it relates to means and methods for protecting toroidal conductivity sensors from biological growth thereon that causes a slow decrease in conductivity readings.

2. Description of the Prior Art

Non-toroidal salinity sensors are particularly susceptible to the deleterious effects of biological growth on the sensors, due in part to the exposed electrodes found in such sensors. The application of anti-foulant chemicals does little to stem the problem, especially in the biologically active lower latitudes.

Toroidal salinity sensors are more resistant to such fouling, but organisms nonetheless grow slowly upon them and eventually cause them to produce erroneous readings. Significantly, the fouling occurs so slowly that the decrease in conductivity falls too gradually to be noticed until the readings are clearly bad. Thus, many months may pass where a sensor is fouled and generating inaccurate readings without the knowledge of those collecting data from it.

What is needed, then, is a salinity sensor that is not subject to fouling by biologically active organisms.

However, in view of the prior art considered as a whole at the time the present invention was made, it was not obvious to those of ordinary skill in the pertinent art how the identified need could be fulfilled.

SUMMARY OF INVENTION

The long-standing but heretofore unfulfilled need for a method and apparatus that protect a toroidal conductivity sensor from fouling is now met by a new, useful, and nonobvious invention. The steps of the method include enclosing the sensor in a hollow enclosure and providing at least one opening in the hollow enclosure to enable water to flow into the hollow enclosure so that the sensor is immersed therein. Biologically active marine organisms are filtered from the water as it flows through the at least one opening to inhibit growth of marine organisms on the sensor. Accordingly, the sensor does not lose its sensitivity due to marine organisms growing thereon.

The structure of the novel apparatus that protects a submerged sensor head from fouling by biologically active marine organisms includes an enclosure having a hollow interior for housing the sensor head. At least one opening is formed in the enclosure to admit water into the hollow interior. A filter is disposed in the at least one opening for removing marine organisms from water admitted into the hollow enclosure. Accordingly, the sensor head is submerged in water that is substantially free of marine organisms.

More particularly, the enclosure includes a tubular base made of a straight pipe, an end cap having a tubular part that ensleeves a first end of the tubular base, and a closure means formed integrally with the tubular part. A first plurality of openings is formed in a preselected part of the end cap and a first plurality of filter means is positioned within each opening of the first plurality of openings.

A coupler has a tubular part that ensleeves a second end of the straight pipe and further includes a diameter-reducing part formed integrally with the tubular part of the coupler. The diameter-reducing part has a frusto-conical configuration. A second plurality of openings is formed in a preselected part of the coupler and a second plurality of filter means is positioned within each opening of the second plurality of openings.

An annular neck extends from the diameter-reducing part. A sensor means includes an elongate base and a sensor head is mounted to a first end of the elongate base. The annular neck is adapted to receive the elongate base therethrough so that the sensor head is positioned within the hollow enclosure.

A clamping means maintains the elongate base against sliding displacement relative to the annular neck so that the sensor head has a fixed position within the hollow enclosure. The clamping means includes a pipe that is split axially to accommodate the elongate base of the sensor means. The elongate base is slideably received within the axially split pipe, and the clamping means further including an annular band adapted to be positioned in overlying relation to the axially split pipe and tightened.

An important object of this invention is to protect a submerged toroidal conductivity sensor from fouling by marine organisms.

A more specific object is to immerse the sensor in a housing to protect it from marine organisms while ensuring that sea water within the hollow interior of the housing has the same conductivity as sea water external to the housing so that the sensor makes true measurements.

Another object is to filter biologically active marine organisms from the sea water that is within the hollow interior of the enclosure.

Another object is to position a toroidal conductivity sensor in sufficient spaced apart relation to metallic or other electrically conductive materials so that such materials do not interfere with measurements made by the sensor.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2 is an elevational view of the enclosure in its assembled configuration and including the toroidal sensor housed therewithin.

DETAILED DESCRIPTION

Figure 1:
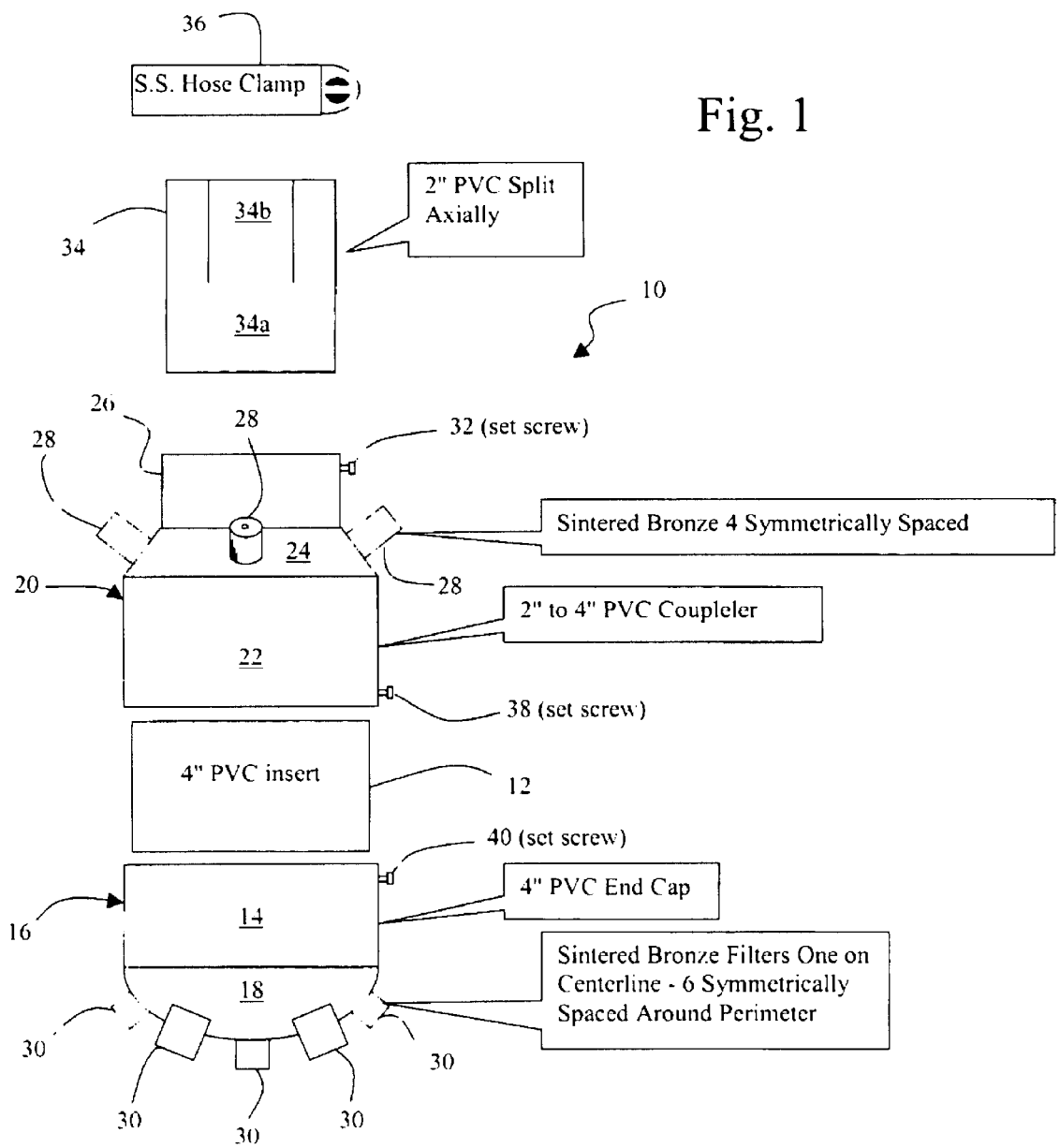
FIG. 1 is an exploded elevational view of the novel enclosure.

Referring to FIG. 1, it will there be seen that the reference numeral 10 denotes an illustrative embodiment of the present invention as a whole.

Enclosure 10 includes a tubular base 12 made of a straight PVC pipe having a diameter of about four inches (4").

A lower or first end of base 12 is ensleeved by tubular part 14 of end cap 16. Closure means 18 is formed integrally with said tubular part 14.

An upper or second end of base 12 is ensleeved by PVC coupler 20. Specifically, coupler 20 includes a first tubular part 22 that ensleeves tubular base . Diameter-reducing part 24 is formed integrally with tubular part 22 and has a frusto-conical configuration so that it reduces the diameter of tubular part 22 to about two inches (2"). Annular neck 26 extends upwardly relative to part 24.

A first plurality of equidistantly and circumferentially spaced filters, collectively denoted 28, is mounted to frusto-conical wall 24 in registration with a first plurality of openings formed in said wall. There are four filters 28 in the illustrated embodiment, only three of which are visible, but four is not a critical number. A second plurality of filters, collectively denoted 30, is mounted on end cap in registration with a second plurality of openings formed in said end cap in the illustrated embodiment, one of the filters 30 is mounted at the center of end cap 18, on the longitudinal axis of symmetry of said end cap, and six additional filters are equidistantly and circumferentially spaced about the perimeter of said end cap. The depicted number and placement of filters 28 and 30 is exemplary and not critical.

Filters 28 and 30 are preferably sintered bronze filters because that material inhibits biological growth and therefore such filters are slow to become clogged. Due to the metallic structure of the filters, it is important to space them apart from the sensor head to avoid false readings. An important feature of this invention is that the sensor head is positioned a maximum distance from the filters, within the limitations of the size of the hollow enclosure.

The surface area of each filter 28 or 30 is preferably sufficiently large to enable free passage of water therethrough. This ensures that the water in the enclosure is the same as the water outside it, with the exception that the water within the enclosure is substantially free of marine organisms.

Set screw 32 screwthreadedly engages an internally threaded radial bore formed in neck 26. A two inch (2") in diameter PVC pipe 34 is split axially and lower end 34a thereof is slideably received within neck 26. Set screw 32 bears against said lower end 34a when said set screw is advanced, thereby securing pipe 34 to neck 26.

When the novel structure is assembled, a toroidal sensor, not depicted in FIG. 1, is slideably received within pipe 34 and hose clamp 36 is tightened around split part 34b of pipe 34 to secure said toroidal sensor against longitudinal displacement.

Set screw 38 serves to join together four inch (4") PVC pipe 12 and tubular part 22, and set screw 40 joins said PVC pipe 12 and tubular part 14. Adhesives may also be employed, either as an auxiliary holding means or in lieu of said set screws.

As depicted in FIG. 2, toroidal sensor 50 includes an elongate base 52, neck 54, and sensor head 56.

Hose clamp 36 and set screws 32, 38, and 40 are eliminated from FIG. 2 to simplify the drawing. Such fastening means are also relatively unimportant because many different fastening means can be employed in lieu thereof or in conjunction therewith.

Significantly, sensor head 56 is positioned in the center of enclosure 10. Accordingly, it is not in physical contact with any part of said enclosure 10. No metal part or other conductor that could interfere with the measurements made by sensor head 56 is in close proximity thereto, thereby attaining an important object of the invention.

The large surface area of filters 28 and 30 enables free water flow into enclosure 10, thereby ensuring that water in the enclosure has the same conductivity as water external to said enclosure, thereby attaining another important object of the invention.

The enclosure prevents marine growth from attaching to sensor head 56, thereby attaining yet another object of the invention. The organisms that attach to the sensor heads of the prior art are filtered out of the water within enclosure 10 by filters 28 and 30.

Base 52 of toroidal sensor 50 is attachable to a tide gauge or any other underwater structure by any suitable means.

Enclosure 10 could be built in many different ways, all of which are obvious to those of ordinary skill in the mechanical arts in view of this disclosure and its teachings relating to the efficacy of enclosing sensor head 56 within a filtered, substantially organism-free submerged environment.

Any sensor head requiring protection from marine organisms may be housed in the novel enclosure, i.e., the invention is not limited to the protection of toroidal conductivity sensors.

Without restriction to any particular apparatus, the novel method for inhibiting growth of marine organisms on a submerged sensor includes the steps of enclosing the sensor in a hollow enclosure, providing a plurality of openings in the hollow enclosure to enable water to flow into the hollow enclosure so that the sensor is immersed therein, and filtering biologically active marine organisms from the water as the water flows through the plurality of openings to inhibit growth of the marine organisms on the sensor.

It will thus be seen that the objects set forth above, and those made apparent from the foregoing description, are efficiently attained, since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method for inhibiting growth of marine organisms on a submerged sensor, comprising the steps of:

enclosing said sensor in a hollow enclosure;

providing at least one opening in said hollow enclosure to enable water to flow into said hollow enclosure so that said sensor is immersed therein; and filtering biologically active marine organisms from said water as it flows through said at least one opening to inhibit growth of said marine organisms on said sensor;

whereby said sensor does not lose its sensitivity due to marine organisms growing thereon.

2. A method for inhibiting growth of marine organisms on a submerged sensor, comprising the steps of:

enclosing said sensor in a hollow enclosure;

providing a plurality of openings in said hollow enclosure to enable water to flow into said hollow enclosure so that said sensor is immersed therein; and filtering biologically active marine from said water as said water flows through said plurality of openings to inhibit growth of said marine organisms on said sensor;

whereby said sensor does not lose its sensitivity due to marine organisms growing thereon.

3. The method of claim 2, wherein said filtering includes filters having electrically conductive parts.

4. The method of claim 2, wherein the step of enclosing said sensor in a hollow enclosure further includes the step of positioning said sensor within said hollow enclosure so that said sensor is sufficiently spaced apart from all filters having electricity-conducting parts to ensure that readings made by said sensor are not influenced by proximity to said filters having electricity-conducting parts.

5. The method of claim 2, wherein said filtering includes filters having sufficient surface area to enable the substantially unrestricted flow of water into said hollow interior.

6. An apparatus that protects a submerged sensor head from fouling by biologically active marine organisms, comprising:

an enclosure having a hollow interior for housing said sensor head;

at least one opening formed in said enclosure to admit water into said hollow interior;

a filter disposed in said at least one opening for removing marine organisms from water admitted into said hollow enclosure;

said sensor head being submerged in said water admitted into said hollow enclosure, said water being substantially free of marine organisms.

7. An apparatus that protects a submerged sensor head from fouling by biologically active marine organisms, comprising:

a hollow enclosure submerged within a body of water;

at least one opening formed in said hollow enclosure so that water flows through said at least one opening into said hollow enclosure when said hollow enclosure is submerged;

a filter means positioned in said at least one opening;

said filter means having sufficient surface area to enable free flow of water through said filter means into said hollow enclosure;

said filter means adapted to capture biologically active marine organisms in said body of water to substantially prevent said organism from entering into said hollow enclosure;

said sensor head positioned within said hollow enclosure in sufficiently spaced relation relative to electricity-conducting surfaces of said enclosure and filter means to substantially inhibit interference with said sensor head by said surfaces.

8. The apparatus of claim 7, wherein said enclosure further comprises:

a tubular base made of a straight pipe;

an end cap having a tubular part that ensleeves a first end of said tubular base;

a closure means formed integrally with said tubular part;

a first plurality of openings formed in a preselected part of said end cap;

a first plurality of filter means positioned within each opening of said first plurality of openings;

a coupler having a tubular part that ensleeves a second end of said straight pipe;

a diameter-reducing part formed integrally with said tubular part of said coupler;

said diameter-reducing part having a frusto-conical configuration;

a second plurality of openings formed in a preselected part of said coupler;

a second plurality of filter means positioned within each opening of said second plurality of openings;

an annular neck extending from said diameter-reducing part;

a sensor means including an elongate base and a sensor head mounted to a first end of said elongate base;

said annular neck adapted to receive said elongate base therethrough so that said sensor head is positioned within said hollow enclosure;

whereby said first and second plurality of filter means enable water to flow into said hollow interior of said enclosure; and whereby said filter means remove marine organisms from the water flowing into said hollow interior.

9. The apparatus of claim 8, further comprising:

clamping means for maintaining said elongate base against sliding displacement relative to said annular neck so that said senor head has a fixed position within said hollow enclosure.

10. The apparatus of claim 9, wherein said clamping means further includes a pipe that is split axially to accommodate said elongate base of said sensor means, said elongate base being slideably received within said axially split pipe and said clamping means further including an annular band adapted to be positioned in overlying relation to said axially split pipe and tightened.

11. The apparatus of claim 8, wherein said filter means includes electricity-conducting parts and wherein said sensor head is positioned within said hollow interior in substantially equidistantly spaced apart relation relative to said filter means to minimize interference with sensor head readings.

* * * * *